United States Patent
Mao et al.

(10) Patent No.: US 10,906,863 B1
(45) Date of Patent: Feb. 2, 2021

(54) HYDROXYTYROSOL 4-METHOXYCINNAMIC ACID ESTER WITH ANTIBACTERIAL ACTIVITY AND A METHOD OF PREPARING THE SAME

(71) Applicants: Gennian Mao, Xi'an (CN); Limei Wang, Xi'an (CN); Bin Tian, Xi'an (CN); Xingke Ju, Xi'an (CN); Nan Hui, Xi'an (CN); Juan Li, Xi'an (CN); Guaiping Qiao, Xi'an (CN); Dan Yang, Xi'an (CN); Jingwen Xu, Xi'an (CN); Liang Qi, Xi'an (CN); Wenbo Yao, Xi'an (CN); Han Li, Xi'an (CN); Chengyuan Liang, Xi'an (CN)

(72) Inventors: Gennian Mao, Xi'an (CN); Limei Wang, Xi'an (CN); Bin Tian, Xi'an (CN); Xingke Ju, Xi'an (CN); Nan Hui, Xi'an (CN); Juan Li, Xi'an (CN); Guaiping Qiao, Xi'an (CN); Dan Yang, Xi'an (CN); Jingwen Xu, Xi'an (CN); Liang Qi, Xi'an (CN); Wenbo Yao, Xi'an (CN); Han Li, Xi'an (CN); Chengyuan Liang, Xi'an (CN)

(73) Assignee: SHAANXI UNIVERSITY OF SCIENCE AND TECHNOLOGY, Xi'an (CN)

(*) Notice: Subject to any disclaimer, the term of this patent is extended or adjusted under 35 U.S.C. 154(b) by 0 days.

(21) Appl. No.: 16/845,028

(22) Filed: Apr. 9, 2020

(51) Int. Cl.
*C07C 69/736* (2006.01)
*C07C 67/08* (2006.01)

(52) U.S. Cl.
CPC .......... *C07C 69/736* (2013.01); *C07C 67/08* (2013.01)

(58) Field of Classification Search
None
See application file for complete search history.

(56) References Cited

PUBLICATIONS

Song ("Synthesis of Diverse Hydroxycinnamoyl Phenylethanoid Esters Using *Escherichia coli*" J. Agric. Food Chem. 2019, 67, p. 2028-2035; including Supporting Information (SI) p. S1-S27) (Year: 2019).*

Shi ("Synthesis of Caffeic Acid Phenethyl Ester Derivatives, and Their Cytoprotective and Neuitogenic Activities in PC12 Cells" J. Agric. Food Chem. 2014, 62, p. 5046-5053) (Year: 2014).*

* cited by examiner

*Primary Examiner* — Amy C Bonaparte

(57) ABSTRACT

A compound having the formula (I):

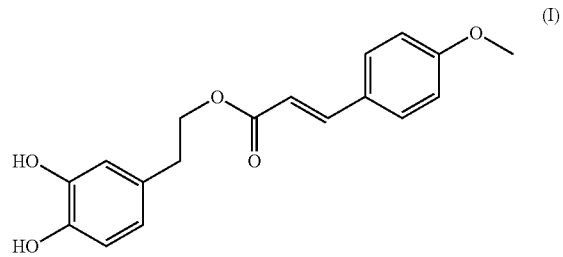

is disclosed. A method of preparing the compound of formula (I) is also disclosed.

1 Claim, 4 Drawing Sheets

HYDROXYTYROSOL 4-METHOXYCINNAMIC ACID ESTER WITH ANTIBACTERIAL ACTIVITY AND A METHOD OF PREPARING THE SAME

FIELD OF THE INVENTION

The present invention relates to the field of medicinal chemistry, more specifically, an ahydroxytyrosol 4-methoxycinnamic acid ester with antibacterial activity and a method of preparing the same.

BACKGROUND OF THE INVENTION

There are different types of antibacterial agents, including β-lactam, aminoglycoside, macrolide, chloramphenicol, glycopeptide, tetracycline, and so on. Over the years, antibacterial resistant bacteria have developed rapidly. The emergence of methicillin-resistant *Staphylococcus aureus* (MRSA), penicillin-resistant *Streptococcus pneumoniae* (PRSP), vancomycin-resistant *Enterococcus* (VRE), extended-spectrum β-lactamase (ESBl), AmpC enzyme and metallo-β-lactamase (MBL) producing strain, multi-drug-resistant *Mycobacterium tuberculosis* (MDRMT) and so on has caused serious difficulties in clinical treatment. At present, both Gram-positive bacteria and Gram-negative bacteria have developed drug resistance, and the problem of drug resistance of Gram-positive bacteria is more serious. There is a need to develop new antibacterial agents that are active against antibacterial resistant bacteria.

Hydroxytyrosol (compound of formula II) is a natural polyphenol compound with a small molecular weight and a yellowish-brown oily liquid. It has a variety of biological and pharmacological activities and can be extracted from olive oil. Hydroxytyrosol plays a role in anti-oxidation, anti-cancer, anti-inflammation, prevention and treatment of cardiovascular and cerebrovascular diseases, prevention and treatment of coronary heart disease, protection of retinal pigment epithelial cells and so on.

4-methoxycinnamic acid (compound of formula III), also known as (4-methoxyphenyl) acrylic acid, is a white amorphous granular powder and a natural phenylpropane compound, which can also be modified by cinnamic acid.

In the present invention, 4-methoxycinnamic acid is modified by hydroxytyrosol to obtain a hydroxytyrosol 4-methoxycinnamic acid ester. Preliminary antibacterial activity experiment shows that the compound has excellent antibacterial activity and has high medical research and application value in the treatment of infectious diseases caused by multidrug resistant bacteria.

SUMMARY OF THE INVENTION

In one embodiment, the present invention provides a compound having the following formula (I):

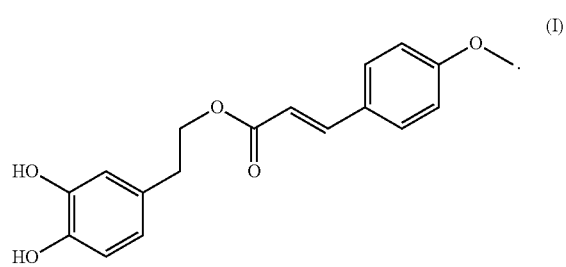 [SMILES: COc1ccc(/C=C/C(=O)OCCc2ccc(O)c(O)c2)cc1]

In another embodiment, the present application provides a method of preparing the compound of formula (I). The method includes: reacting a compound of formula (II) with a compound of formula (III) to obtain the compound of formula (I):

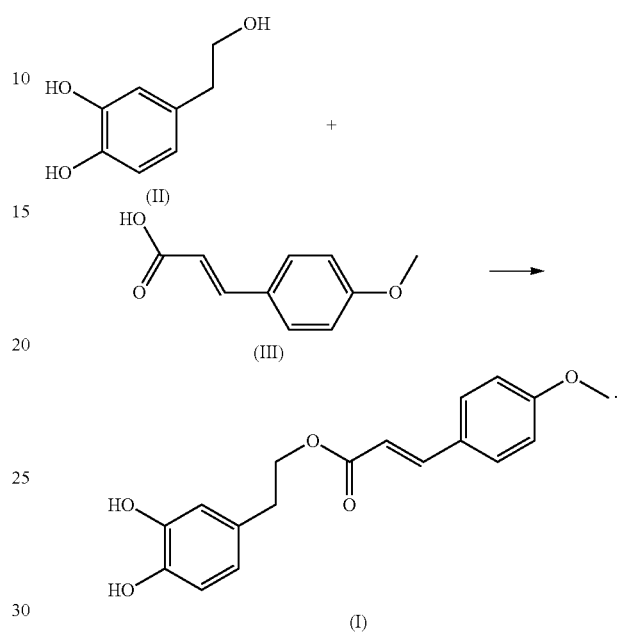

In another embodiment, the reaction of the compound of formula (II) with the compound of formula (III) includes the following steps: placing a compound of formula (II) and a compound of formula (III), in a molar ratio of 1:1 to 1:1.3, in a reactor; adding an organic solvent and a catalytic amount of EDC under nitrogen atmosphere to obtain a reaction mixture; heating the reaction mixture at 50-80° C. for 8-12 hours; concentrating the reaction mixture to give a crude product; and purifying the crude product on a silica gel fresh chromatography column with petroleum ether and ethyl acetate as an eluent to obtain the compound of formula (I).

In another embodiment, the organic solvent is toluene, ethyl acetate or acetonitrile.

In another embodiment, the organic solvent is acetonitrile.

In another embodiment, the molar ratio of the compound of formula (II) and the compound of formula (III) is 1:1.1.

In another embodiment, the reaction mixture is heated at 80° C.

In another embodiment, the reaction mixture is heated for 10 hours.

In another embodiment, the eluent is petroleum ether: ethyl acetate=1:3.

In another embodiment, the reaction of the compound of formula (II) with the compound of formula (III) includes the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 30-50° C. for 5-10 hours; placing the reaction mixture in a separating funnel to separate a crude product; purifying the crude product by recrystallization in methanol to obtain the compound of formula (I); and recycling the ionic liquid.

In another embodiment, the ionic liquid is 1-butyl-3-methylimidazolium tetrafluoroborate ([BMIM][BF$_4$]).

In another embodiment, the compound of formula (II) and the compound (III) have a molar ratio of 1:1 to 1:1.3.

In another embodiment, the molar ratio of the compound of formula (II) and the compound of formula (III) is 1:1.1.

In another embodiment, the reaction mixture is heated at 30° C.

In another embodiment, the reaction mixture is heated for 8 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
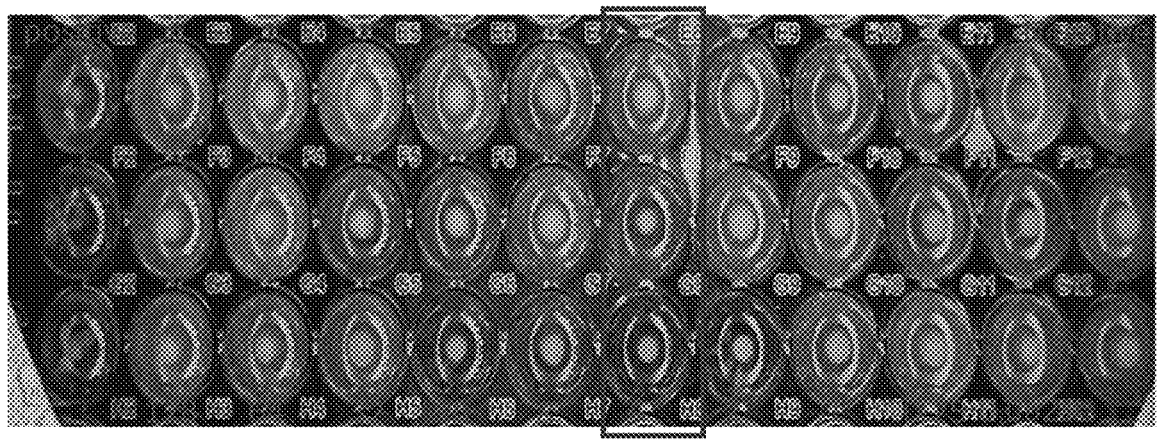
FIG. 1 shows the results of in vitro antibacterial activity of hydroxytyrosol 4-methoxycinnamic acid ester against drug-resistant bacteria MARS 18-222.

Reference will now be made in detail to embodiments of the present invention, example of which is illustrated in the accompanying drawings. The following examples illustrate the present invention, but the present invention is not limited to the following examples.

Example 1: Preparation of Compound (E)-3,4-dihydroxyphenethyl 3-(4-methoxyphenyl)acrylate (Compound of Formula I)

In a 200 mL three-necked flask, 100.1 mg (0.65 mmol) of hydroxytyrosol and 124.0 mg (0.65 mmol) EDC (1-ethyl-3-(3-dimethylaminopropyl)carbodiimide) were dissolved in 50 mL of acetonitrile under nitrogen atmosphere. 126.7 mg (0.71 mmol) of 4-methoxycinnamic acid was dissolved in 20 mL of acetonitrile, and slowly added dropwise to the reaction liquid by a separatory funnel. After the completion of the dropwise addition, the temperature was raised to 80° C., and the reaction was carried out for 10 hours. Thin layer chromatography was used to track the reaction to completion, heating was stopped, and the protective device was removed. The concentrated solution was washed in water, extracted with chloroform, dried and concentrated, and a crude product was obtained. The crude product was further purified by silica gel column chromatography, petroleum ether:ethyl acetate=1:3 as eluent, and the eluent was concentrated under reduced pressure and dried to obtain the title compound, 145.8 mg, a yield of 75.36%.

$^1$H-NMR (400 MHz, DMSO-d$_6$) δ (ppm): 7.75 (2H, d), 7.42 (1H, s), 6.94 (2H, d), 6.76 (1H, s), 6.72 (1H, d), 6.64 (1H, d), 6.32 (1H, s), 5.32 (2H, s), 4.48 (2H, t), 3.75 (3H, s), 2.63 (2H, t); $^{13}$C-NMR (400 MHz, DMSO-d$_6$) (δ ppm): 167.8, 155.6, 140.5, 127.5, 126.2, 123.5, 118.8, 112.2, 111.9, 110.2, 61.3, 50.8, 30.9.

Example 2: Preparation of Compound (E)-3,4-dihydroxyphenethyl 3-(4-methoxyphenyl)acrylate In a 200 mL three-necked flask, 100.1 mg (0.65 mmol) of hydroxytyrosol and 124.0 mg (0.65 mmol) EDC were dissolved in 50 mL of toluene under nitrogen atmosphere. 126.5 mg (0.71 mmol) of 4-methoxycinnamic acid was dissolved in 20 mL of toluene, and slowly added dropwise to the reaction liquid by a separatory funnel. After the completion of the dropwise addition, the temperature was raised to 60° C., and the reaction was carried out for 12 hours. Thin layer chromatography was used to track the reaction to completion, heating was stopped, and the protective device was removed. The concentrated solution was washed in water, extracted with chloroform, dried and concentrated, and a crude product was obtained. The crude product was further purified by silica gel column chromatography, petroleum ether:ethyl acetate=1:3 as eluent, and the eluent was concentrated under reduced pressure and dried to obtain the title compound, 131.7 mg, a yield of 64.08%.

Example 3: Preparation of Compound (E)-3,4-dihydroxyphenethyl 3-(4-methoxyphenyl)acrylate In a 200 mL three-necked flask, 100.1 mg (0.65 mmol) of hydroxytyrosol and 124.0 mg (0.65 mmol) EDC were dissolved in 50 mL of ethyl acetate under nitrogen atmosphere. 126.5 mg (0.71 mmol) of 4-methoxycinnamic acid was dissolved in 20 mL of ethyl acetate, and slowly added dropwise to the reaction liquid by a separatory funnel. After the completion of the dropwise addition, the temperature was raised to 60° C., and the reaction was carried out for 12 hours. Thin layer chromatography was used to track the reaction to completion, heating was stopped, and the protective device was removed. The concentrated solution was washed in water, extracted with chloroform, dried and concentrated, and a crude product was obtained. The crude product was further purified by silica gel column chromatography, petroleum ether:ethyl acetate=1:3 as eluent, and the eluent was concentrated under reduced pressure and dried to obtain the title compound, 125.1 mg, a yield of 61.23%.

Example 4: Preparation of Compound (E)-3,4-dihydroxyphenethyl 3-(4-methoxyphenyl)acrylate In a 200 mL three-necked flask, 100.1 mg (0.65 mmol) of hydroxytyrosol and 124.0 mg (0.65 mmol) EDC were dissolved in 50 mL of acetonitrile under nitrogen atmosphere. 139.0 mg (0.78 mmol) of 4-methoxycinnamic acid was dissolved in 20 mL of acetonitrile, and slowly added dropwise to the reaction liquid by a separatory funnel. After the completion of the dropwise addition, the temperature was raised to 70° C., and the reaction was carried out for 12 hours. Thin layer chromatography was used to track the reaction to completion, heating was stopped, and the protective device was removed. The concentrated solution was washed in water, extracted with chloroform, dried and concentrated, and a crude product was obtained. The crude product was further purified by silica gel column chromatography, petroleum ether:ethyl acetate=1:3 as eluent, and the eluent was concentrated under reduced pressure and dried to obtain the title compound, 139.5 mg, a yield of 68.28%.

Example 5: Preparation of Compound (E)-3,4-dihydroxyphenethyl 3-(4-methoxyphenyl)acrylate In a 200 mL three-necked flask, 100.1 mg (0.65 mmol) of hydroxytyrosol and 124.0 mg (0.65 mmol) EDC were dissolved in 50 mL of toluene under nitrogen atmosphere. 151.6 mg (0.85 mmol) of 4-methoxycinnamic acid was dissolved in 20 mL of toluene, and slowly added dropwise to the reaction liquid by a separatory funnel. After the completion of the dropwise addition, the temperature was raised to 80° C., and the reaction was carried out for 8 hours. Thin layer chromatography was used to track the reaction to completion, heating was stopped, and the protective device was removed. The concentrated solution was washed in water, extracted with chloroform, dried and concentrated, and a crude product was obtained. The crude product was further purified by silica gel column chromatography, petroleum ether:ethyl acetate=1:3 as eluent, and the eluent was concentrated under reduced pressure and dried to obtain the title compound, 128.1 mg, a yield of 62.70%.

Example 6: Preparation of Compound (E)-3,4-dihydroxyphenethyl 3-(4-methoxyphenyl)acrylate In a 200 mL three-necked flask, 100.1 mg (0.65 mmol) of hydroxytyrosol and 124.0 mg (0.65 mmol) EDC were dissolved in 50 mL of ethyl acetate under nitrogen atmosphere. 139.1 mg (0.78 mmol) of 4-methoxycinnamic acid was dissolved in 20 mL of ethyl acetate, and slowly added dropwise to the reaction liquid by a separatory funnel. After the completion of the dropwise addition, the temperature was raised to 70° C., and the reaction was carried out for 10 hours. Thin layer chromatography was used to track the reaction to completion, heating was stopped, and the protective device was removed. The concentrated solution was washed in water, extracted with chloroform, dried and concentrated, and a crude product was obtained. The crude product was further purified by silica gel column chromatography, petroleum ether:ethyl acetate=1:3 as eluent, and the eluent was concentrated under reduced pressure and dried to obtain the title compound, 118.7 mg, a yield of 58.10%.

Example 7: Preparation of Compound (E)-3,4-dihydroxyphenethyl 3-(4-methoxyphenyl)acrylate In a 100 mL three-necked flask, 100.1 mg (0.65 mmol) of hydroxytyrosol, 126.5 mg (0.71 mmol) of 4-methoxycinnamic acid and 12.0 mg (0.007 mmol) silicomolybdic acid were dissolved in 50 mL of 1-butyl-3-methylimidazolium tetrafluoroborate under nitrogen atmosphere. After full dissolution, the temperature was raised to 30° C. and the reaction was carried out for 8 hours. Thin layer chromatography was used to track the reaction to completion, heating was stopped, and the protective device was removed. The reaction mixture system was allowed to separate into layers to give a crude product. The crude product was recrystallized with 50 mL methanol and dried to obtain the title compound, 174.6 mg, a yield of 85.51%.

Example 8: Preparation of Compound (E)-3,4-dihydroxyphenethyl 3-(4-methoxyphenyl)acrylate In a 100 mL three-necked flask, 100.1 mg (0.65 mmol) of hydroxytyrosol, 126.5 mg (0.71 mmol) of 4-methoxycinnamic acid and 12.0 mg (0.007 mmol) silicomolybdic acid were dissolved in 50 mL of 1-butyl-3-methylimidazolium tetrafluoroborate under nitrogen atmosphere. After full dissolution, the temperature was raised to 50° C. and the reaction was carried out for 10 hours. Thin layer chromatography was used to track the reaction to completion, heating was stopped, and the protective device was removed. The reaction mixture system was allowed to separate into layers to give a crude product. The crude product was recrystallized with 50 mL methanol and dried to obtain the title compound, 163.0 mg, a yield of 79.83%.

Example 9: Antibacterial Activity Test of the Compound of Formula I

The minimal inhibitory concentration (MIC) of the compound as determined by a microbroth dilution method with gentamicin, cefazolin sodium and ceftriaxone sodium as positive control.

The experimental strains included methicillin-resistant Gram-positive bacteria: methicillin-resistant *Staphylococcus aureus* MRSA 18-222, 18-575; multiple drug-resistant Gram-negative bacteria: vancomycin-resistant enterococci VRE 18-80,18-94, multidrug-resistant *Pseudomonas aeruginosa* MDR-PA 18-1774,18-202, carbapenem-resistant *Acinetobacter baumannii* CR-AB 18-183,18-560. All the experimental strains were donated by Huashan Hospital affiliated to Fudan University (Institute of antibiotics, Fudan University) and used after routine identification.

Preparation of Test Strains:

Preparation of MHB medium: 20.0 g MHB medium was added to 1 L distilled water, boiled until completely dissolved, packed in conical bottles and sterilized at 121° C. for 15 min.

The experimental strain was cultured to the logarithmic growth phase: under aseptic condition, the experimental strain was inoculated into 100 mL MHB medium and incubated in a constant temperature and humidity incubator at 37° C. for 20-22 hours.

Preparation of storage solution: weigh the sample to be tested, dissolve it with 1% DMSO solution, prepare a storage solution with a concentration of 2560 μg/mL, weigh a positive reference substance, dissolve it with aseptic distilled water, and configure a storage solution with a concentration of 2560 μg/mL.

Preparation of Bacterial Suspension:

Under aseptic condition, the experimental strains cultured to logarithmic growth phase were adjusted to 0.5 MCF turbidity standard with MHB medium and diluted according to 1:10, and the bacterial suspension with concentration of $10^6$ CFU/mL was prepared for standby.

Dilution of storage solution and inoculation of experimental strain: under aseptic condition, the storage solution was diluted to 256 μg/mL solution. Take a sterile 96-well plate, add 200 μL MHB medium to the 12th well, and add 100 μL MHB medium to each well. Add 100 μL of positive control solution to the first well, mix well, and suck 100 μL from it and discard. Add 100 μL of the compound sample solution to the second well, mix well, and then pipette 100 μL to the third well. After mixing, pipette 100 μL to the fourth well, and dilute to the 11th well in this way. Finally, 100 μL was pipetted from the 11th well and discarded. The 12th hole was the growth control without drugs. So far, the concentration of the positive reference substance is 128 μg/mL, the concentrations of the sample solution are 128, 64, 16, 8, 4, 2, 1, 0.5, 0.25 μg/mL respectively. Then, 10 μL of the prepared bacterial suspension is added to each well, so that the final concentration of the bacterial liquid in each well is $5 \times 10^5$ CFU/mL.

Incubation: Cover the 96-well plate inoculated with the experimental strains, and incubate in a constant temperature and humidity box at 37° C. for 20-22 hours.

Interpretation of the MIC endpoint: The concentration that can completely inhibit the growth of bacteria in a 96-well plate under a black background is the lowest inhibitory concentration of the sample against the bacteria.

Figure 2:
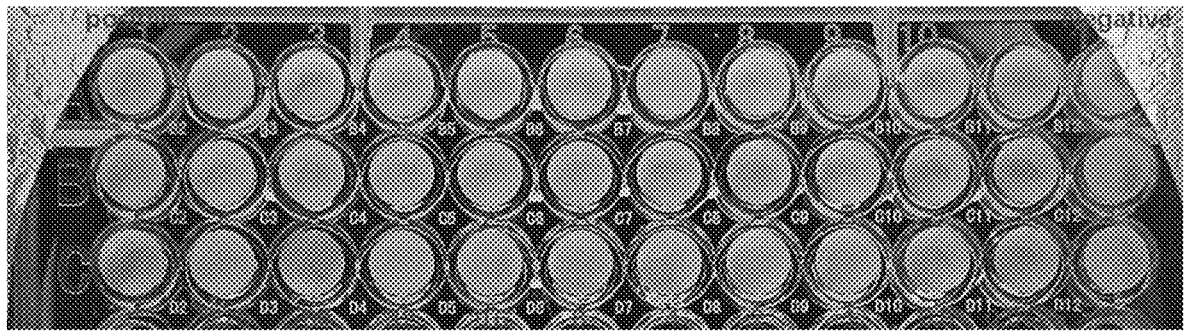
FIG. 2 shows the results of in vitro antibacterial activity of Cefazolin sodium against drug-resistant bacteria MARS 18-222.
Figure 3:
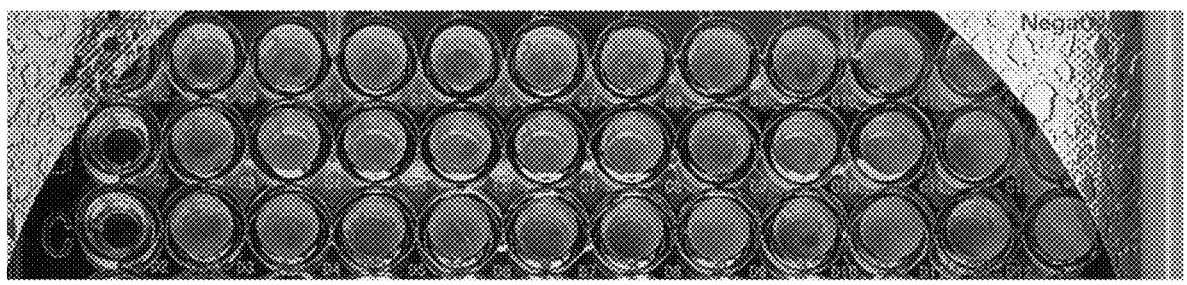
FIG. 3 shows the results of in vitro antibacterial activity of hydroxytyrosol against drug-resistant bacteria MARS 18-222.
Figure 4:
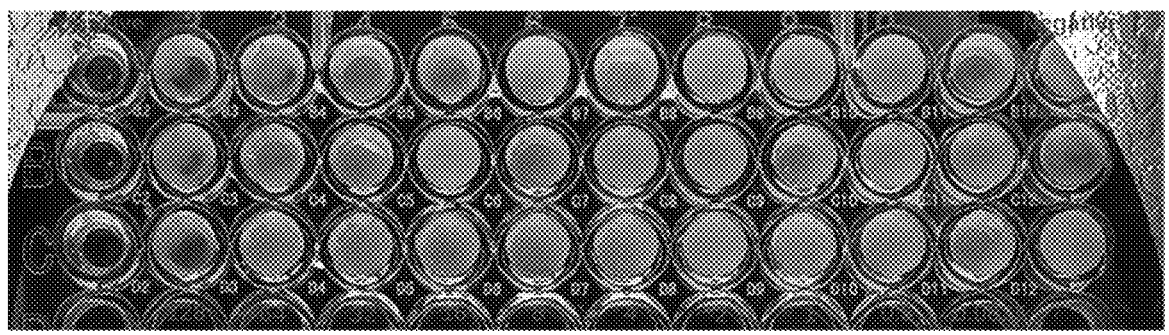
FIG. 4 shows the results of in vitro antibacterial activity of 4-methoxycinnamic acid against drug-resistant bacteria MARS 18-222.
Figure 5:
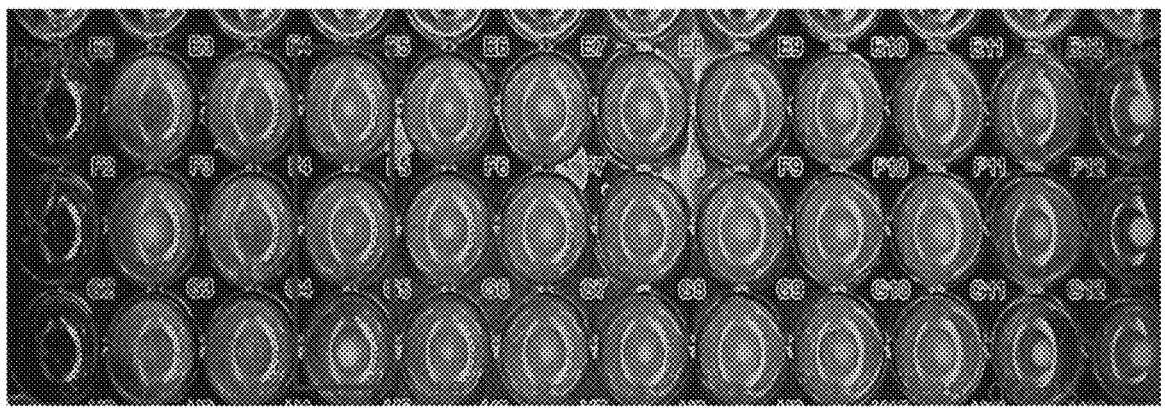
FIG. 5 shows the results of in vitro antibacterial activity of hydroxytyrosol 4-methoxycinnamic acid ester against drug-resistant bacteria MARS 18-575.
Figure 6:
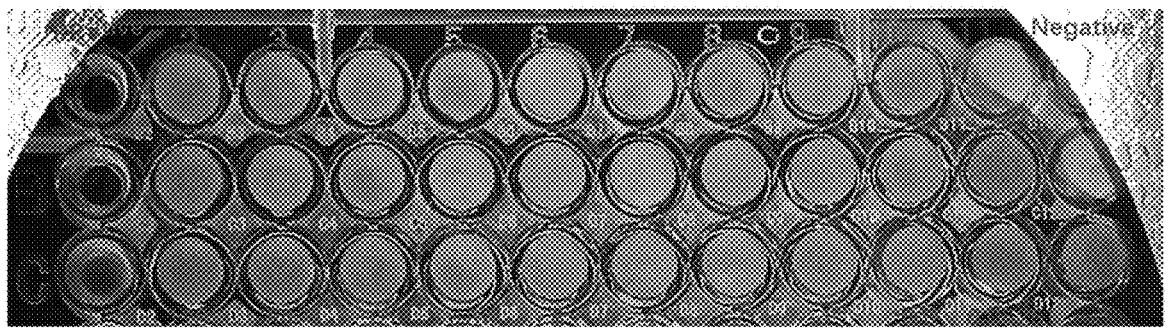
FIG. 6 shows the results of in vitro antibacterial activity of hydroxytyrosol against drug-resistant bacteria MARS 18-575.
Figure 7:
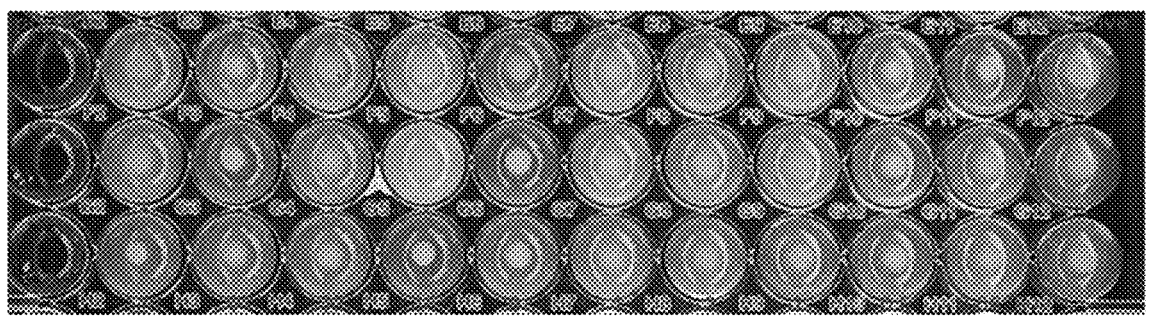
FIG. 7 shows the results of in vitro antibacterial activity of 4-methoxycinnamic acid against drug-resistant bacteria MARS 18-575.
Figure 8:
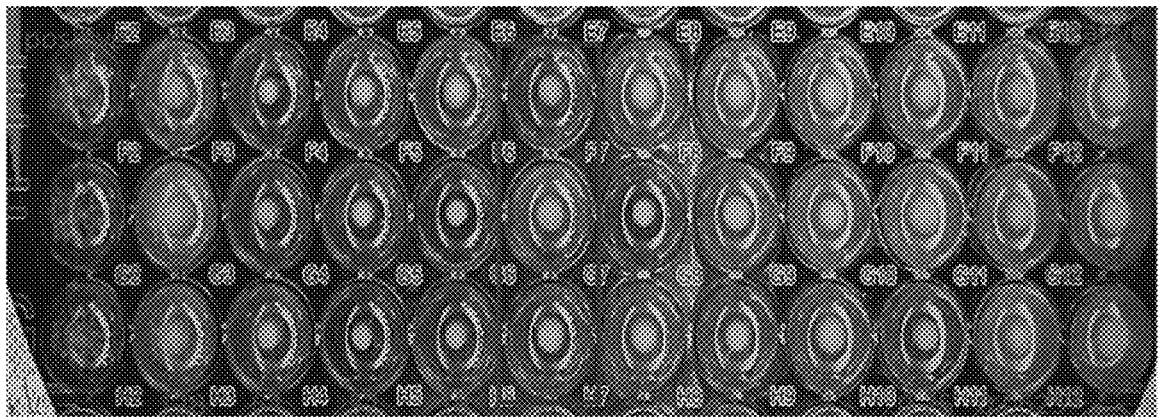
FIG. 8 shows the results of in vitro antibacterial activity of hydroxytyrosol 4-methoxycinnamic acid ester against drug-resistant bacteria MDR-PA 18-174.
Figure 9:
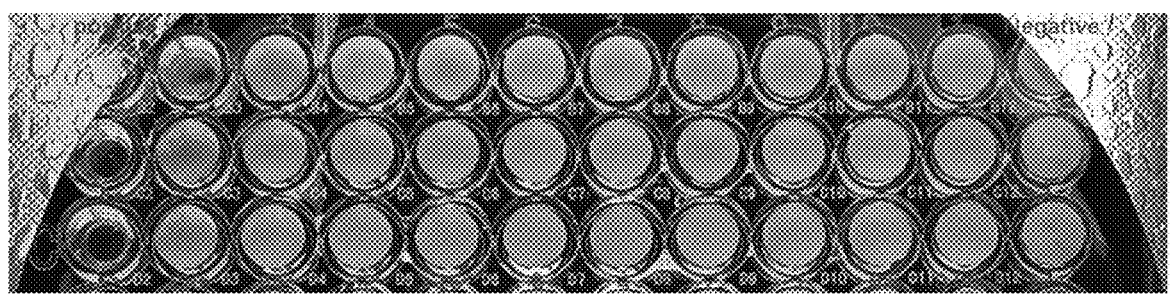
FIG. 9 shows the results of in vitro antibacterial activity of hydroxytyrosol against drug-resistant bacteria MDR-PA 18-174.
Figure 10:
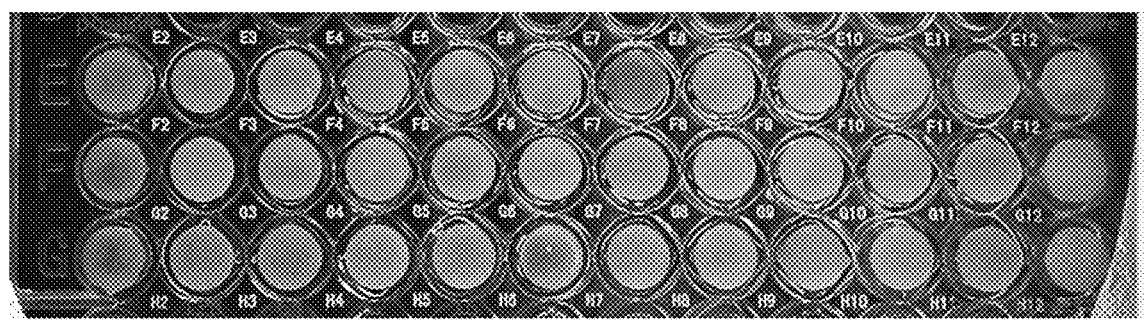
FIG. 10 shows the results of in vitro antibacterial activity of 4-methoxycinnamic acid against drug-resistant bacteria MDR-PA 18-174.

In FIGS. 1-10, the twelve wells represent twelve groups, from left to right, positive, 128 μg/mL, 64 μg/mL, 32 μg/mL, 16 μg/mL, 8 μg/mL, 4 μg/mL, 2 μg/mL, 1 μg/mL, 0.25 μg/mL, 0.0625 μg/mL, Negative. FIG. 1 shows the in vitro antibacterial activity of hydroxytyrosol 4-methoxycinnamic acid ester against drug-resistant bacteria MARS 18-222. FIG. 2 shows the in vitro antibacterial activity of Cefazolin sodium against drug-resistant bacteria MARS 18-222. FIG. 3 shows the in vitro antibacterial activity of hydroxytyrosol against drug-resistant bacteria MARS 18-222. FIG. 4 shows the in vitro antibacterial activity of 4-methoxycinnamic acid against drug-resistant bacteria MARS 18-222. FIG. 5 shows the in vitro antibacterial activity of hydroxytyrosol 4-methoxycinnamic acid ester against drug-resistant bacteria MARS 18-575. FIG. 6 shows the in vitro antibacterial activity of hydroxytyrosol against drug-resistant bacteria MARS 18-575. FIG. 7 shows the in vitro antibacterial activity of 4-methoxycinnamic acid against drug-resistant bacteria MARS 18-575. FIG. 8 shows the in vitro antibacterial activity of hydroxytyrosol 4-methoxycinnamic acid ester against drug-resistant bacteria MDR-PA 18-174. FIG. 9 shows the in vitro antibacterial activity of hydroxytyrosol against drug-resistant bacteria MDR-PA 18-174. FIG. 10 shows the in vitro antibacterial activity of 4-methoxycinnamic acid against drug-resistant bacteria MDR-PA 18-174. The results are summarized in Table 1.

TABLE 1

Minimum Bacteriostatic Concentration of Test Compound and Positive Controls (μg · mL$^{-1}$)

| | Strain | | | | | | | |
|---|---|---|---|---|---|---|---|---|
| | MRSA | | VRE | | MDR-PA | | CR-AB | |
| Sample | 18-222 | 18-575 | 18-80 | 18-94 | 18-174 | 18-202 | 18-183 | 18-560 |
| Hydroxytyrosol 4-methoxycinnamic acid ester | 4 | 32 | >128 | >128 | 8 | >128 | >128 | >128 |
| Gentamicin | 128 | 2 | 0.0625 | >128 | 0.0625 | 0.0625 | >128 | >128 |
| Cefazolin sodium | >128 | >128 | 32 | >128 | 8 | 128 | >128 | >128 |
| Ceftriaxone sodium | >128 | >128 | 8 | >128 | 128 | 16 | >128 | >128 |
| Hydroxytyrosol | >128 | >128 | >128 | >128 | >128 | >128 | >128 | >128 |
| 4-methoxycinnamic acid | >128 | >128 | >128 | >128 | >128 | >128 | >128 | >128 |

According to the experimental results of FIG. 1-10 and Table 1, hydroxytyrosol and 4-methoxycinnamic acid have no inhibitory effect on drug-resistant bacteria, while hydroxytyrosol 4-methoxycinnamic acid ester derivative has strong inhibitory effect on drug-resistant Gram-positive bacteria MRSA (MIC=4 μg/mL) and MDR-PA (MIC=8 μg/mL), even stronger than that of positive control drugs. In summary, the hydroxytyrosol 4-methoxycinnamic acid ester of the invention can be used as an antibacterial candidate for Gram-positive bacteria methicillin-resistant *Staphylococcus aureus* and multi-drug-resistant *Pseudomonas aeruginosa*, and further preclinical research.

What is claimed is:

1. A method of preparing a compound of formula (I), comprising:
    reacting a compound of formula (II) with a compound of formula (III) to obtain the compound of formula (I):

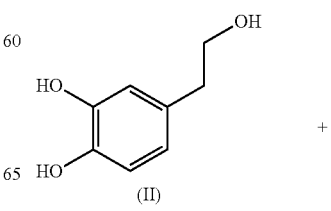

(II)

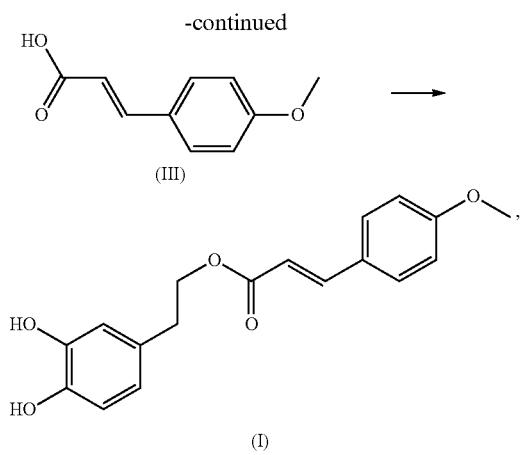

wherein the reaction of the compound of formula (II) with the compound of formula (III) comprises the following steps:

placing the compound of formula (II), a catalyst, and 1-butyl-3-methylimidazolium tetrafluoroborate ([BMIM][BF$_4$]) in a reactor under nitrogen atmosphere, the catalyst being 12-molybdosilicic acid hydrate (H$_6$Mo$_{12}$O$_{41}$Si);

adding the compound of formula (III) to the reactor to form a reaction mixture, the compound of formula (II) and the compound (III) having a molar ratio of 1:1.1;

heating the reaction mixture at 30° C. for 8 hours;

placing the reaction mixture in a separating funnel to separate a crude product;

purifying the crude product by recrystallization in methanol to obtain the compound of formula (I); and recycling 1-butyl-3-methylimidazolium tetrafluoroborate.

\* \* \* \* \*